United States Patent [19]

Sawai et al.

[11] Patent Number: 5,340,806
[45] Date of Patent: Aug. 23, 1994

[54] COMPOSITION CONTAINING ORGANOGERMANIUM COMPOUND AND IMMUNITY ADJUSTING AGENT COMPRISING THE COMPOSITION

[75] Inventors: Kiichi Sawai, Funabashi; Masayasu Kurono; Juichi Awaya, both of Nagoya; Akio Kojima, Kasugai; Hideaki Ninomiya; Yoshiro Ishiwata, both of Nagoya; Masahiro Nakajima, Gifu, all of Japan

[73] Assignee: Sanwa Kagaku Kenkyusho Co., Ltd., Nagoya, Japan

[21] Appl. No.: 850,720

[22] Filed: Jan. 7, 1993

Related U.S. Application Data

[63] Continuation-in-part of Ser. No. 428,675, Oct. 30, 1989, abandoned, which is a continuation-in-part of Ser. No. 224,279, Jul. 25, 1988, Pat. No. 4,889,715, which is a continuation of Ser. No. 809,819, Dec. 17, 1985, abandoned.

[30] Foreign Application Priority Data

Dec. 25, 1984 [JP] Japan ................... 59-272057

[51] Int. Cl.$^5$ ................... A61K 31/79; A61K 31/555; A61K 31/28
[52] U.S. Cl. ................... 514/184; 514/492; 424/78.37
[58] Field of Search ................ 514/184, 492; 424/78.8

[56] References Cited

U.S. PATENT DOCUMENTS 4,889,715 12/1989 Sawai et al. .......................... 424/80

Primary Examiner—Nathan M. Nutter

Attorney, Agent, or Firm—Nikaido, Marmelstein, Murray & Oram

[57] ABSTRACT

A composition comprising an organogermanium compound represented by the formula

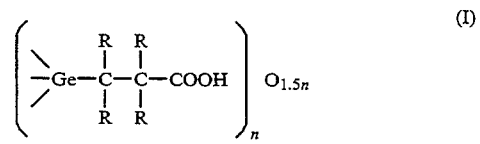

wherein n is an integer of 1 or more, R is hydrogen, alkyl, —COOH, —COOR', phenyl,

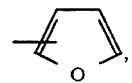

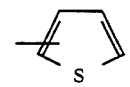

or

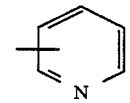

and R' is a lower alkyl and a high molecular carrier, as well as an immunity adjusting agent comprising the composition. The treatment of hepatitis with compositions containing this germanium derivative.

6 Claims, 14 Drawing Sheets

COMPOSITION CONTAINING ORGANOGERMANIUM COMPOUND AND IMMUNITY ADJUSTING AGENT COMPRISING THE COMPOSITION

This application is a continuation in part of application Ser. No. 07/428,675, filed Oct. 30, 1989 and now abandoned, now pending, which is in turn a continuation in part of application Ser. No. 07/224,279 filed Jul. 25, 1988, now U.S. Pat. No. 4,889,715, which is in turn a continuation of application Ser. No. 06/809,819, filed Dec. 17, 1985, now abandoned.

BACKGROUND OF THE INVENTION

1. Field of the Invention

The present invention relates to a composition containing an organogermanium compound and an immunity adjusting agent comprising this composition. The organogermanium compound is represented by the formula:

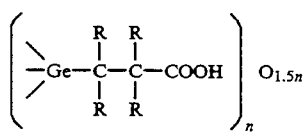 (I)

wherein n is an integer of 1 or more, R is hydrogen, alkyl, —COOH, —COOR', phenyl,

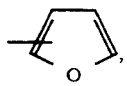,

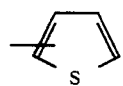

or

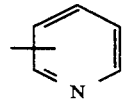

and R' is a lower alkyl.

2. Related Arts

The organogermanium compounds (polymers) represented by Formula I has been watched with great interest in recent years, due to its attractive pharmacological activities, and thus various derivatives of these polymers have been synthesized.

However, these organogermanium compounds as proposed have a common disadvantage in that they are not too stable to water. When such an organogermanium compound is prepared, through the hydrolysis of trichlorogermylpropionic acid, a group of different organogermanium compounds will be formed, as disclosed in Examined Jap. Pat. Appln. Gazette Nos. 2498/1971 and 53800/1982, as well as Unexamined Jap. Pat. Appln. Gazette No. 102895/1982. This means that the product of this hydrolysis will be different, depending on slight differences in the time or conditions of the hydrolysis reaction. Therefore, it is possible to estimate that a certain hydrolysis product may change into another product when the former is suspended or dissolved in water. This phenomenon has actually been reported (Examined Jap. Pat. Appln. Gazette Nos. 53800/1982 and 18399/1984).

The inventors have carefully studied the pharmacological activities of the various organogermanium compounds represented by said Formula I, which have been prepared by a common process, but under a different synthesis conditions, to find that each compound shows a remarkable difference in its degree of pharmacological activity. Now, it is, of course, desired to obtain specific organogermanium compounds which show a high and stable pharmacological activity, in order to utilize them as an effective component of a pharmaceutical agent. However, it has further been confirmed by the inventors, with respect to the compounds of Formula I, and more particularly those wherein all of the substituents R in the Formula are hydrogen, that their degree of polymerization varies due to slight differences in the conditions of synthesis thereof. It has also been determined that, for use as pharmaceutical agents, these compounds should only be in the solid form, because an intermolecular bond therein is easily severed or broken due to a slight change in environment or atmosphere. It has been found that the pharmacological activities inherent in these compounds are not stable, since at least partial decomposition thereof occurs prior to their reaching a desired absorption area in a living body.

Hitherto, a large number of reports, to the effect that the organogermanium compounds in question have an immunity accelerating action as one of its pharmacological properties, have been issued, but all of such compounds have not been employed for developing a pharmaceutical agent, due to their low stability and other difficulties. Some of them have also been considered as a harmful substance to various diseases or disorders concerning to the immunity acceleration system.

However, the inventors have now found, through their various studies, that the organogermanium compounds in question show great effectivity on various immunity disorders, namely both disordered of the immunity inhibition system and the immunity acceleration disorders, and thus the "immunity accelerating action" which has hitherto widely been reported and accepted is not correct and should be corrected to refer to an—immunity adjusting or regulating action—.

OBJECT AND SUMMARY OF THE INVENTION

Therefore, an object of the invention is to provide a composition in which at least one of the compounds of Formula I is physicochemically and pharmacologically stabilized.

Another object of the invention is to provide an immunity adjusting agent useful as a therapeutic agent for treating various immunity disorders due to an abnormal increase or decrease of immunity function in living bodies.

According to the invention, these objects can be attained by a composition comprising an organogermanium compound represented by the formula:

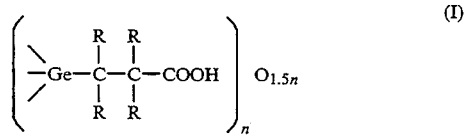

wherein R has the meaning as referred to above, and a high molecular carrier for pharmaceutical agents. This invention also comprises an immunity adjusting agent comprising the composition.

The organogermanium compound of which the composition or the immunity adjusting agent is comprised according to the invention, can be obtained by treating germanium dioxide with *hydro-phosphorous acid or a salt thereof in a halogenohydroacid; reacting the resulting *halogeno-germanium-phosphoric acid complex with a compound represented by the formula:

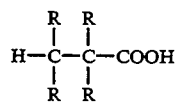
(II)

wherein R has the meaning as referred to above; dissolving the resulting compound represented by the formula:

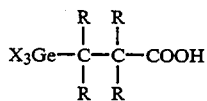
(III)

wherein R has the meaning as referred to above and X is a halogen, into acetone or another organic solvent having a solubility in water, and adding water into the solution.

The high molecular carrier contained in the composition or the immunity adjusting agent, according to the invention, serves also to stabilize the organogermanium compound as the main component. Naturally occurring high molecular substances, synthetic high molecular substances, proteinic substances or *saccharoids may be employed therefor. It is preferable to utilise the carrier in an amount ranging from 0.01 to 200 parts by weight, for instance 0.05 to 5 parts by weight, based on 1 weight part of the organogermanium compound. As the natural high molecular substance, biological one, for instance gelatin, pepsin, serum albumin (cattle, horse or human origin), globulin, *protamine or mixtures thereof may be listed. As the synthetic high molecular substances, polyethylene glycol and the like glycols; *hydroxypropyl-cellulose, hydroxypropylmethylcellulose and the like cellulosic high molecular substances, polyvinylpyrrolidone and the like *vinylic high molecular substances; and polyacrylamide and the like acrylic high molecular substances may be listed. As the proteinic high molecular substances, in general, additives for culture mediums, for instance peptone, polypeptone, yeast extract, tryptone, *tryptose, dextrose and the like may be listed. As the *saccharoid, lactose, refined sugar, glucose, starch, cellulose and the like may be listed.

The compounds as shown in following Table 1 way be listed as exemplary organogermanium compounds to be employed for the invention.

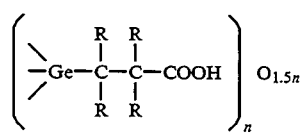
(I)

TABLE 1

| Compound number | $R_1$ | $R_2$ | $R_3$ | $R_4$ | Crystal form and dec. temperature |
|---|---|---|---|---|---|
| 1 | H | H | H | H | white needle, 240° C. |
| 2 | $CH_3$ | H | H | H | white crystal, more than 300° C. |
| 3 | $C_2H_s$ | H | H | H | white crystal, more than 300° C. |
| 4 | $(CH_2)_2CH_3$ | H | H | H | white crystal, more than 300° C. |
| 5 | $(CH_2)_4CH_3$ | H | H | H | white crystal, more than 300° C. |
| 6 | $(CH_2)_{12}CH_3$ | H | H | H | white crystal, 172–176° C. |
| 7 | H | H | $CH_3$ | H | white needle, more then 300° C. |
| 8 | H | H | $C_2H_s$ | H | white crystal, more than 300° C. |
| 9 | $CH_3$ | H | $CH_3$ | H | white crystal, more than 300° C. |
| 10 | $CH_3$ | $CH_3$ | H | H | white crystal, more than 300° C. |
| 11 | COOH | H | H | H | white crystal, more than 300° C. |
| 12 | $C_6H_s$ | H | H | H | white crystal, more than 300° C. |

For making the composition into a pharmaceutical agent, a filling, binder, disintegrator and the like aids may be added, but such air should not have any substantial reactivity to the organogermanium compound, which is used as the main component, and should show no activity in a delayed type immunity response reaction test, from a pharmacological view point.

The pharmaceutical agent may be put up in a composition which will provide a solid delivery system such as for instance: a tablet, capsule, granule, infinitesimal grain, powder, suppository, dry syrup or the like; a solution delivery system, for instance: an injection, oral dosing solution agent, external lotion or the like; or a semi-solid delivery system, for instance an externally applied cream, jelly or the like.

It is preferable for human use to provide a dose in an amount of 0.3 to 20 mg/kg, for instance 1 mg/kg, as the amount of the organogermanium compound.

EFFECT OR ADVANTAGE OF THE INVENTION

According to the invention, the organogermanium compound, used as the main component, is effectively stabilized to allow free selection of the dosing form of the pharmaceutical agent, so that pharmacological activities of the organogermanium compound can efficiently be utilized.

The immunity adjusting agent of the invention shows a powerful and stable physiological activity through an immunity system and is useful as a curing agent for various self immunity disorders such as a tumor, vital disease, phlegmasia, hepatopathy, nephropathy, collagenosis and the like, as well as being an inhibiting agent to a negative reaction which is possibly caused in organ implanting. Of particular significance is the use of the immunity adjusting agent of this invention in the treatment of acquired immune deficiency syndrome (AIDS) and hepatitis.

BRIEF DESCRIPTION OF THE DRAWINGS

FIG. 1 is the IR spectrum of an original or non-treated compound;

FIG. 2 is the IR spectrum of a composition comprising the original compound and a serum albumin, which has been held for 30 days;

FIG. 3 is the IR spectrum of a composition comprising the original compound and gamma-globulin <<γ-globulin>>, which has been held for 30 days;

FIG. 5 is the IR spectrum of a composition comprising the original compound and pepsin, which has been held for 30 days;

FIGS. 6 and 7 are the IR spectra of 4% aqueous solutions of the original compound, which have been helf for 24 and 60 hours, respectively;

FIGS. 8, 8a and 8b are graphs showing the influence of the compound on the ability to produce antibodies, when normal mice are sensitized with SRBC of $2 \times 10^8$ and $2 \times 10^7$, respectively;

DETAILED DESCRIPTION OF PREFERRED EMBODIMENTS

The invention will now be explained with reference to stability test examples, pharmacological test examples and pharmaceutical agent preparation examples.

STABILITY TESTS

1) Physicochemical Stability Test a) To 5 ml of 4% cattle serum albumin solution, 200 mg of the organogermanium compound (Compound No. 1 in Table 1) were added and dispersed therein by a mixer to prepare a composition according to the invention (4% suspension of the organogermanium compound).

The suspension was stored in a thermostat kept at 25° C, sampled out after a lapsed time of 1, 3, 9, 15 and 30 days and filtered. Each resulting solid substance was washed with acetone and ethanol, and then dried for 1 hour at 105° C.

The stability of the resulting dried substance was checked by measuring its IR spectrum, using the potassium bromide tablet method.

Figure 1:
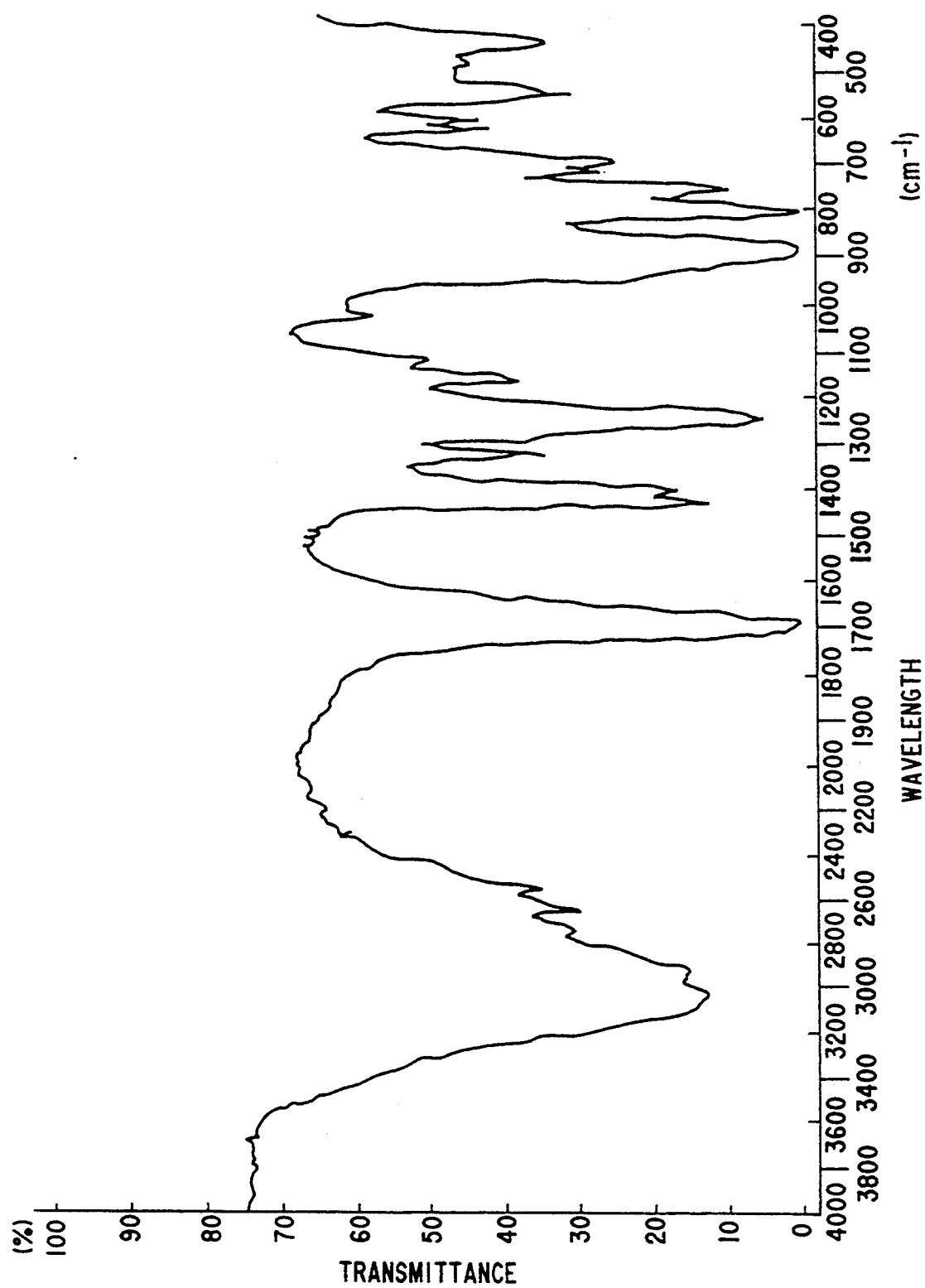
FIGS. 1–7 are graphs showing IR spectra of an organogermanium compound as employed for the present invention, in which—

An IR spectrum of the original or non-treated 15 organogermanium compound is shown in FIG. 1 and has characteristic absorption spectra at 1695, 1435, 1255, 890 and 805 cm$^{-1}$. The stability of each sample in question was judged on the basis of comparison with this characteristic absorption spectrum.

Figure 2:
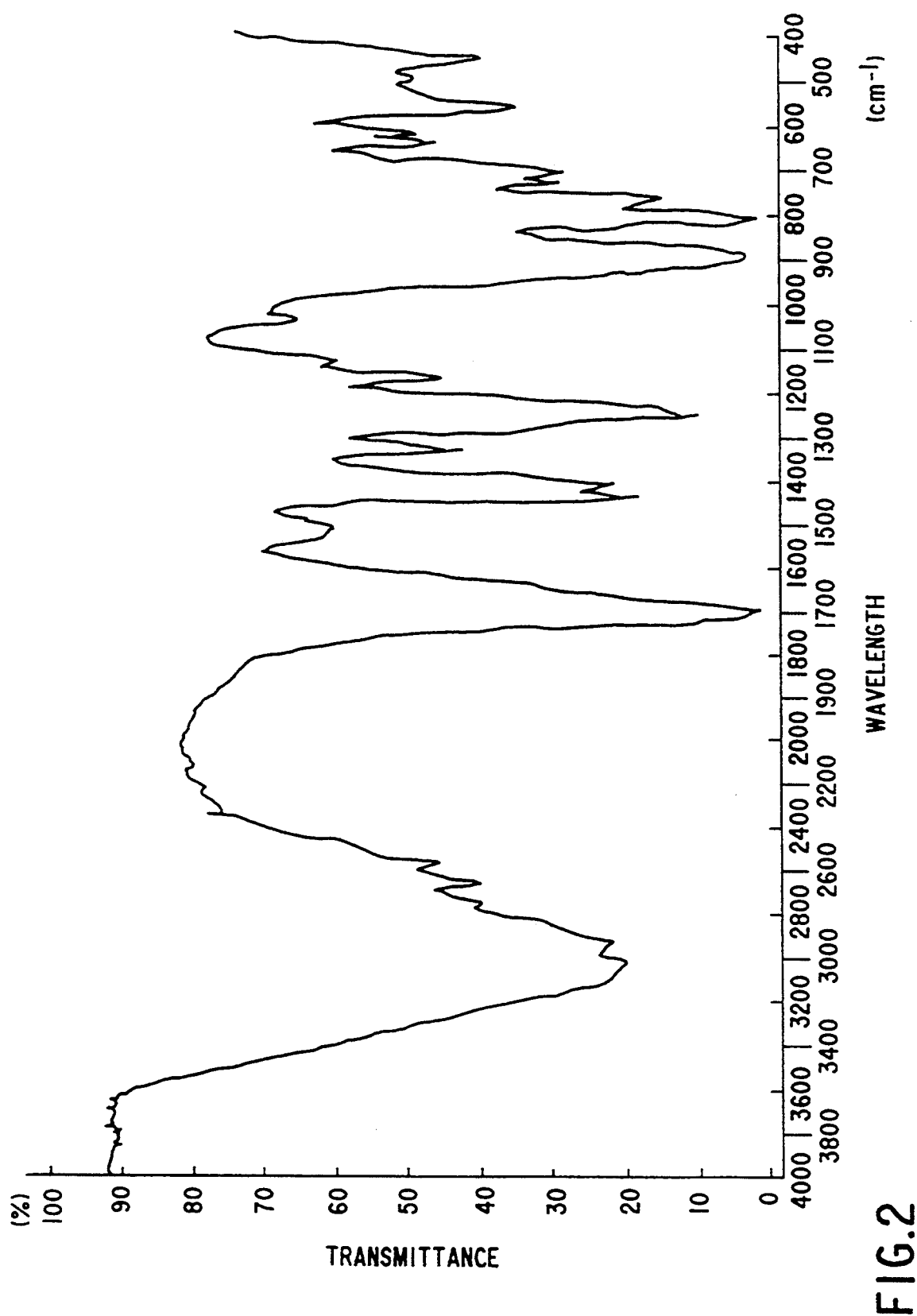

The tested composition maintained its stable state, even after a time lapse of 30 days (see FIG. 2).

Figure 3:
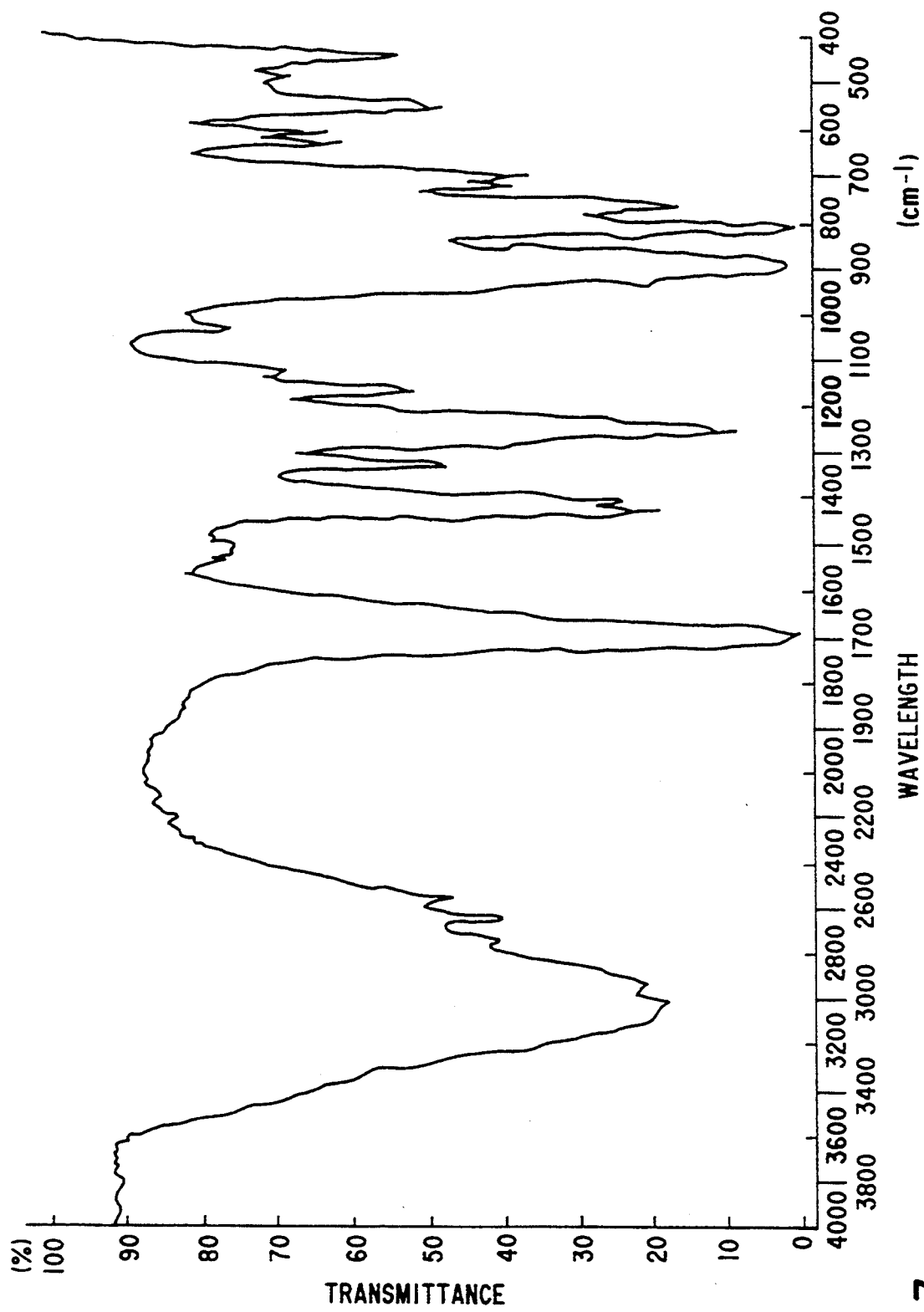
Figure 4:
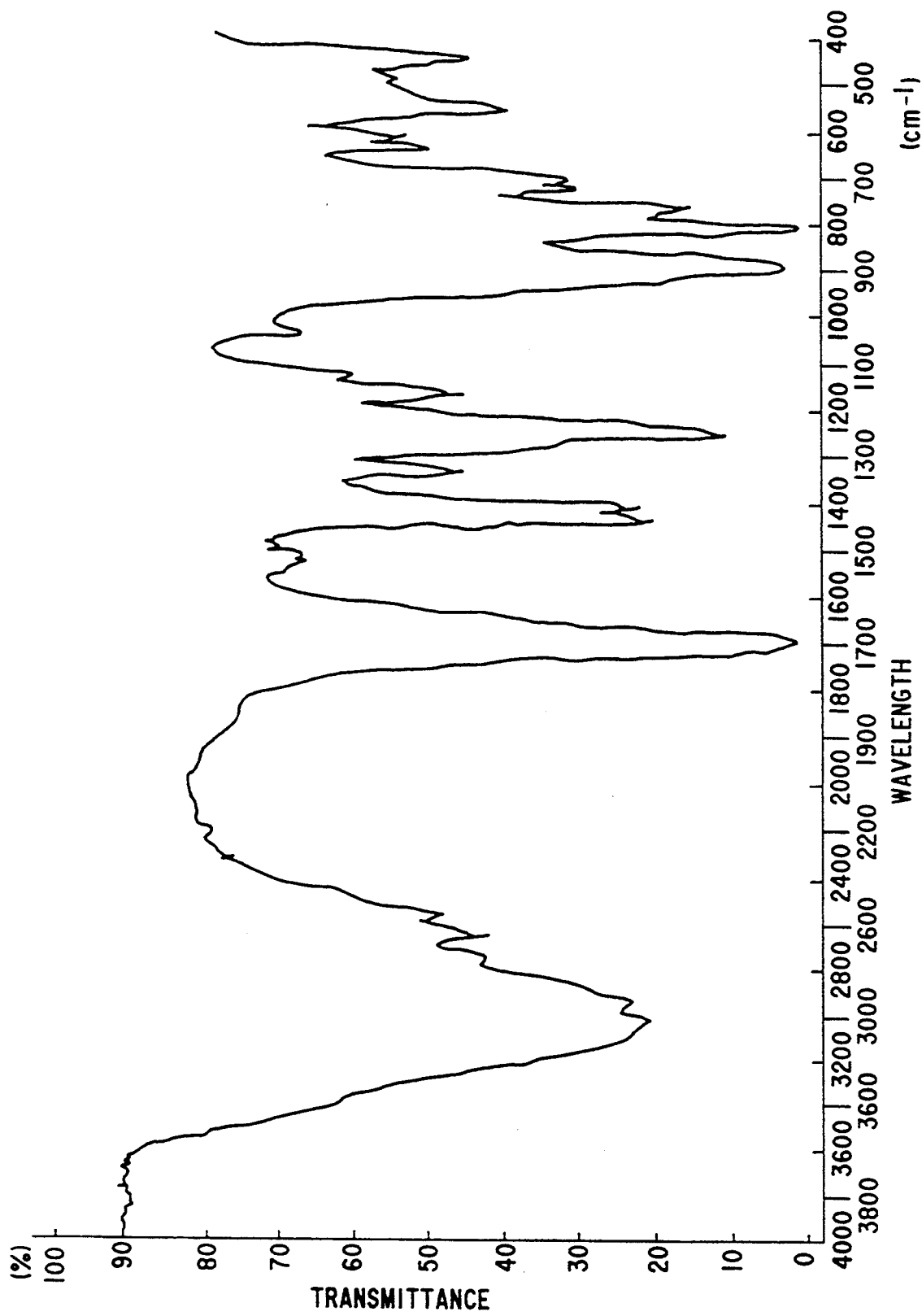
Figure 5:
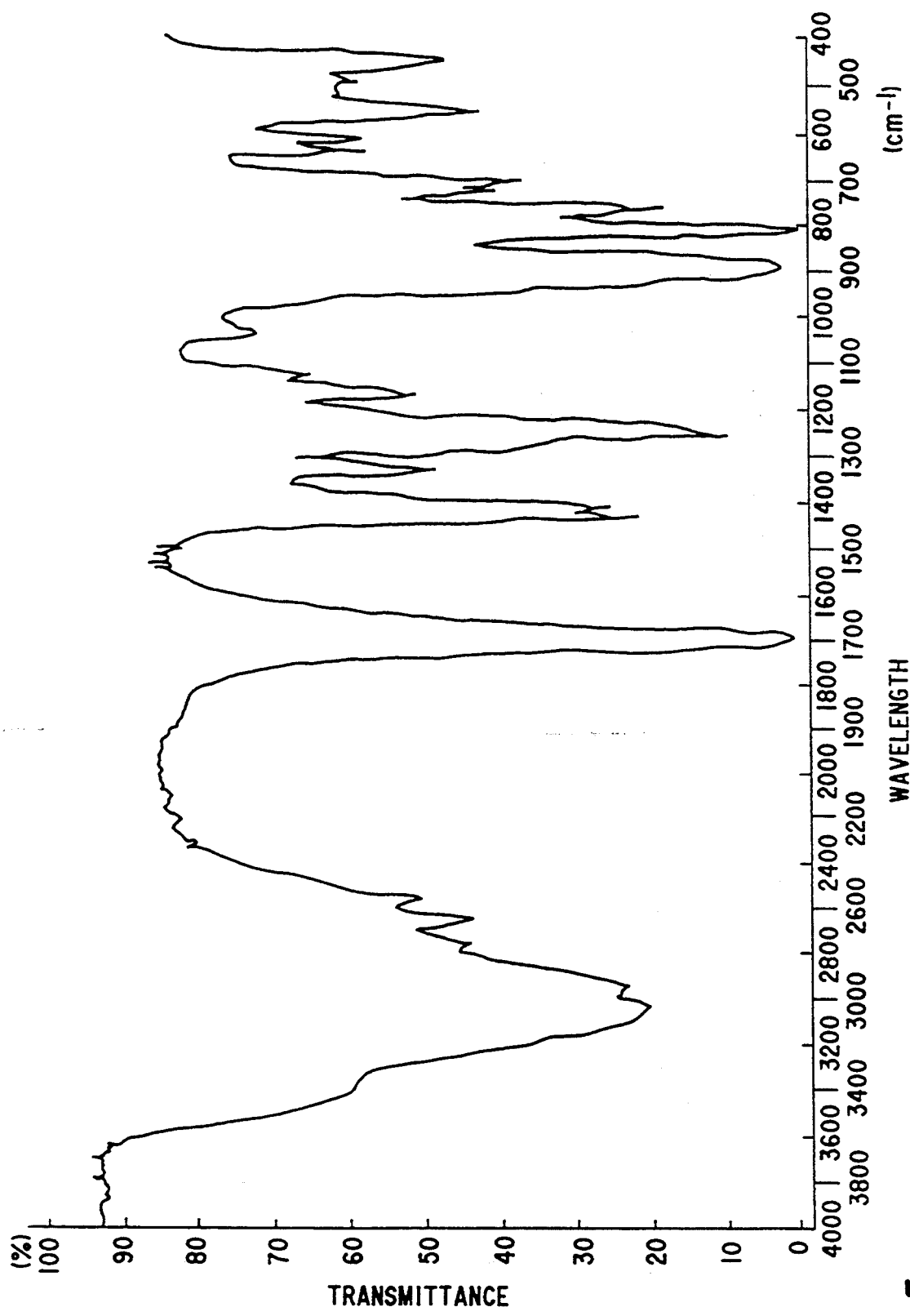
Figure 6:
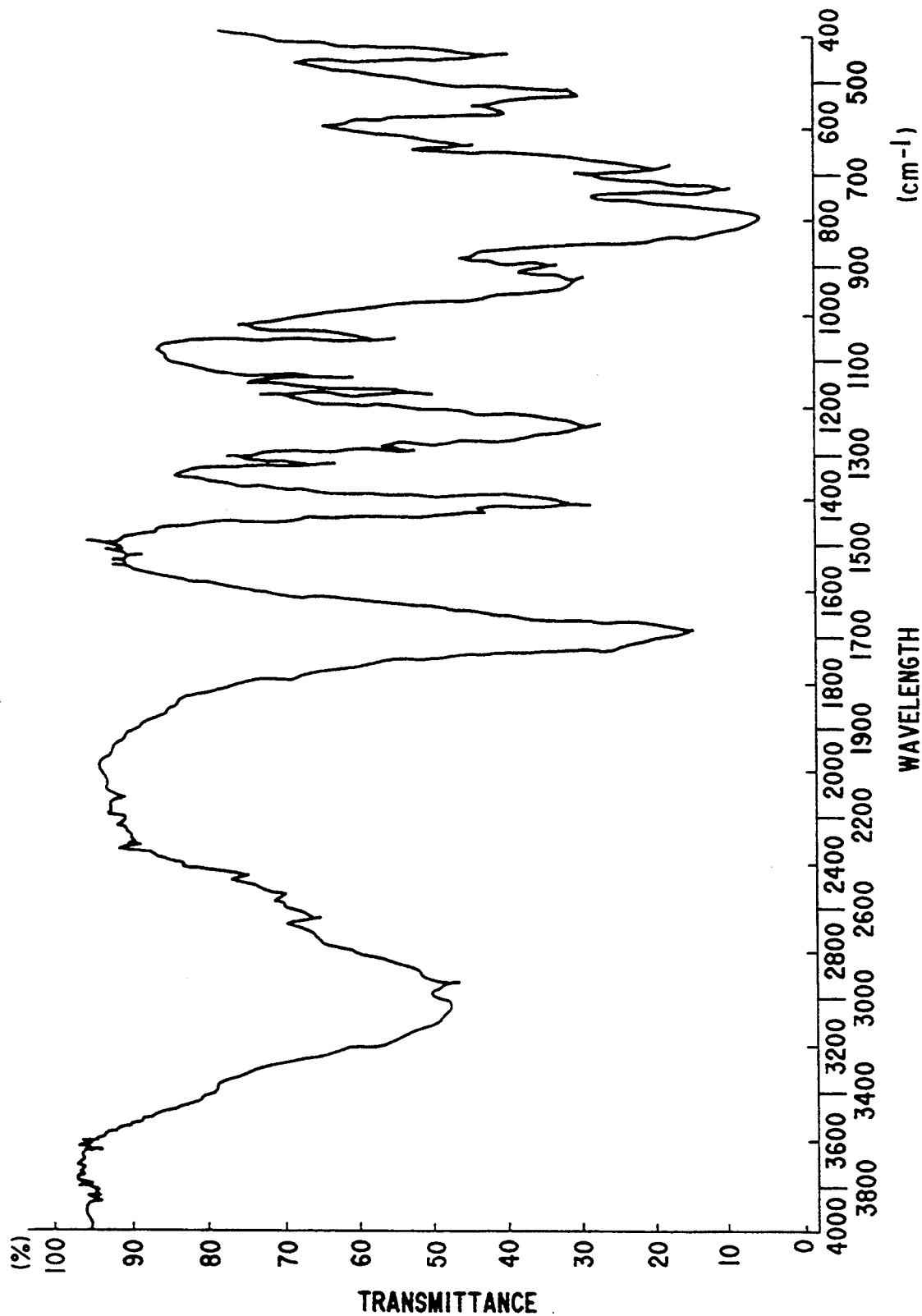
Figure 7:
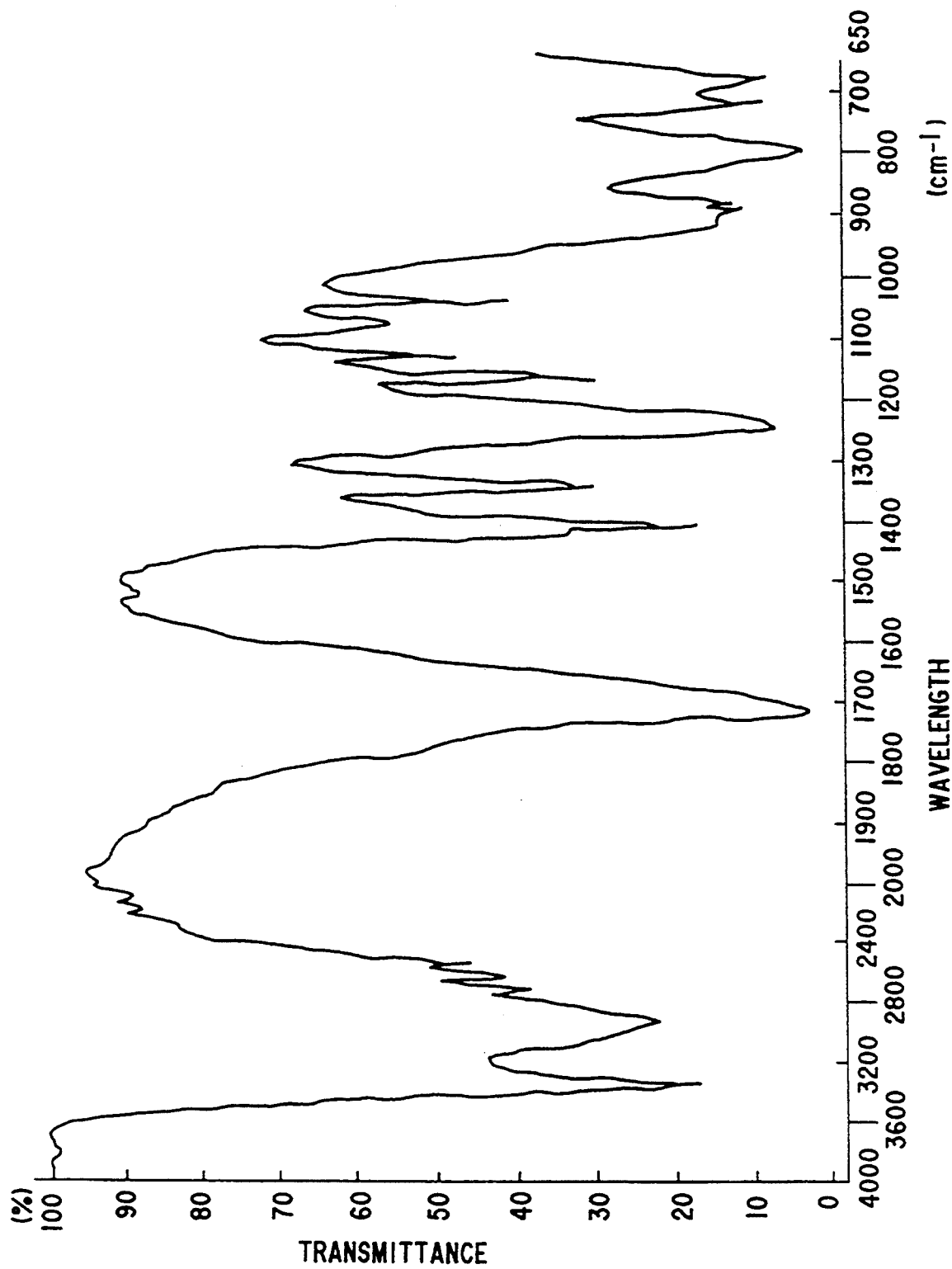

As control, a composition was prepared with use of water in lieu of the serum albumin and its stability was measured in a manner similar to the above to find that a disturbance in the absorption spectrum was first observed on the sample having a lapsed time of 24 hours (see FIG. 6) and that the disturbance was further increased on the sample after a lapsed time of 60 hours (see FIG. 7). This shows that a modification or decomposition occurs in the organogermanium compound in contact with water in the control composition.

b) Compositions according to the invention were prepared as in the case of said Item a but with use of hydroxypropylcellulose, gamma-globulin <<γ-globulin>> and pepsin, respectively, in lieu of the serum albumin. Each of the compositions was tested in the same manner as said Item a to find that the organogermanium compound maintains its stable state, by virtue of its coexistence with the high molecular weight carrier (see FIGS. 3 to 5).

A similar result was obtained on various compositions, wherein gelatin, protamine, hydroxypropylmethylcellulose, polyvinylpyrrolidone, polyacrylamide, peptone, polypeptone, yeast extract, trypton, tryptose, dextrose, lactose, refined sugar, glucose, starch or cellulose were employed as the high molecular carrier for the organogermanium compound, in lieu of the serum albumin.

2. Biological Stability Test

Effect on delayed type *hyperergy (DTH) on cancered mouse.

After implantation of $10^6$ cells of sarcoma 180 cancer cell in an abdominal canal of ICR mice, $10^6$ corpuscles of sheep red blood corpuscle (SRBC) were intravenously injected for sensitization. After a lapsed time of 4 days from the implantation, $2 \times 10^8$ cells of SRBC were injected into the heel of a hind leg of said mice to cause the DTH. After 24 hours from the dosage, the degree of swelling was checked by measuring the thickness of the heel.

On the other hand, various testing compositions (Nos. 1 to 10 in following Table 2) were prepared with use of various high molecular carriers and adding the organogermanium compound thereto (Compound No. 1 in said Table 1), so as to make its concentration of 1 mg/10 ml, and a control testing composition which was prepared by adding the organogermanium compound to water to make its concentration of 1 mg/10 ml. Each of the compositions was orally dosed to each mouse, respectively, 4 days before the cancer cell (Sarcoma 180) implantation, in an amount of 1 mg/10 ml/kg.

Results are shown in the following Table 2. From the table, it can be seen that each of the compositions according to the invention increases the DTH of the cancered mouse, but the control composition is not effective in the dosing amount of 1 mg/kg.

TABLE 2

| | heel swelling (×0.01 mm) mean value ± standard deviation value |
|---|---|
| Non-treated | 114.1 ± 11.5 |
| Cancered | 57.2 ± 7.6 |
| Control composition | 57.0 ± 6.3 |
| Composition of the invention | |
| No. 1 (5% cattle serum albumin) | 75.3 ± 6.3 |
| No. 2 (0.5% gelatin) | 99.9 ± 7.3 |
| No. 3 (1% pepsin) | 109.5 ± 9.2 |
| No. 4 (cattle fetal serum) | 100.8 ± 8.4 |
| No. 5 (10% horse serum albumin) | 96.15 ± 5.6 |
| No. 6 (0.5% polyethylene glycol) | 105.2 ± 8.2 |
| No. 7 (0.5% hydroxypropylcellulose) | 98.3 ± 5.8 |
| No. 8 (0.5% polyvinylpyrrolidone) | 108.3 ± 2.1 |
| No. 9 (0.5% polyacrylamide) | 113.1 ± 2.8 |
| No. 10 (1% peptone) | 92.6 ± 5.4 |

PHARMACOLOGICAL TEST EXAMPLE 1

Influence of Organogermanium Compound on Antibody Production Ability in Normal Mouse a) Object The effect of the organogermanium compound (compound No. 1 in Table 1) is checked by sensitizing mice with an antibody in an amount sufficient to generate sufficient antigen excitement to develop an immunity response at maximum level or not develop a sufficient immunity response due to insufficient antigen excitement.

b) operation

To each group of ICR mice (age, 5 weeks), $2 \times 10^8$ and $2 \times 10^7$ of sheep red blood corpuscles (SRBC), as an antibody, were venously injected for sensitization in a tail vein of the mice. Then, immediately, the organogermanium compound dissolved in 4% cattle serum albumin solution was orally dosed to the sensitized mice in an amount of 0.1, 1.0 and 10 mg/kg, respectively. After 4 days from the sensitization, spleen cells were extracted to measure the number of PFC therein, which was used as an index of the antibody productivity.

Figure 8A:
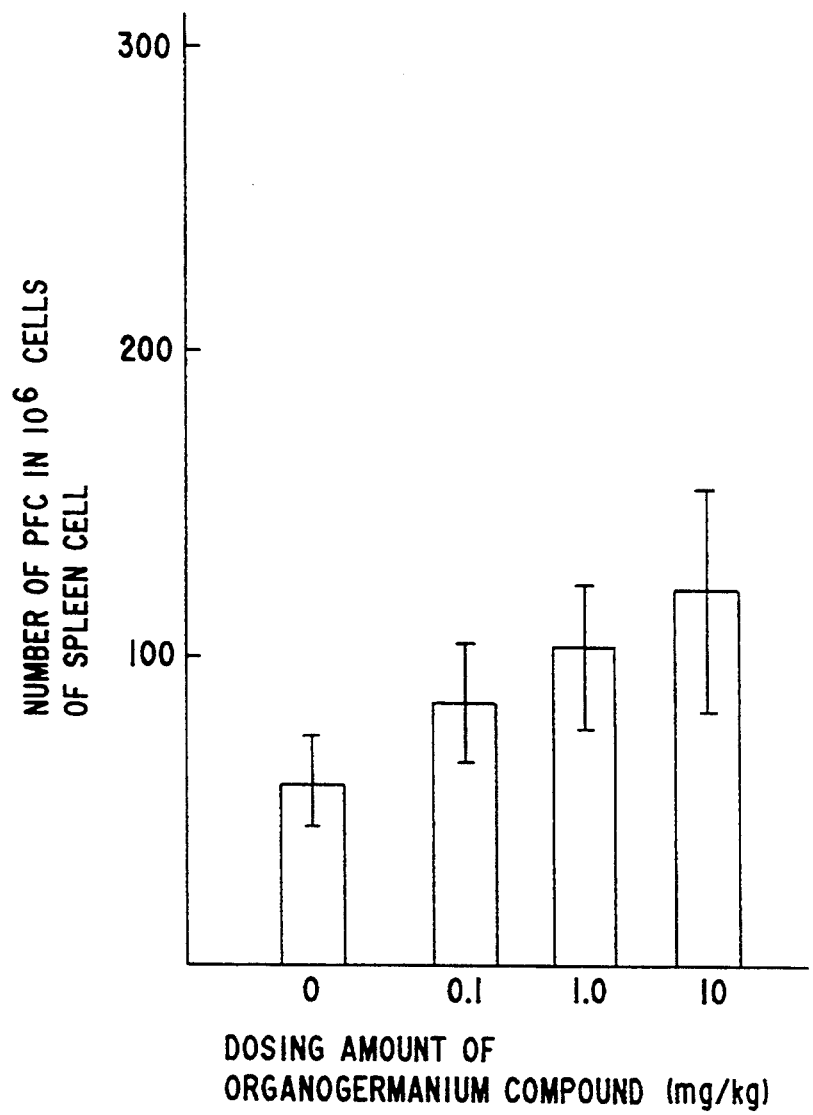
Figure 8B:
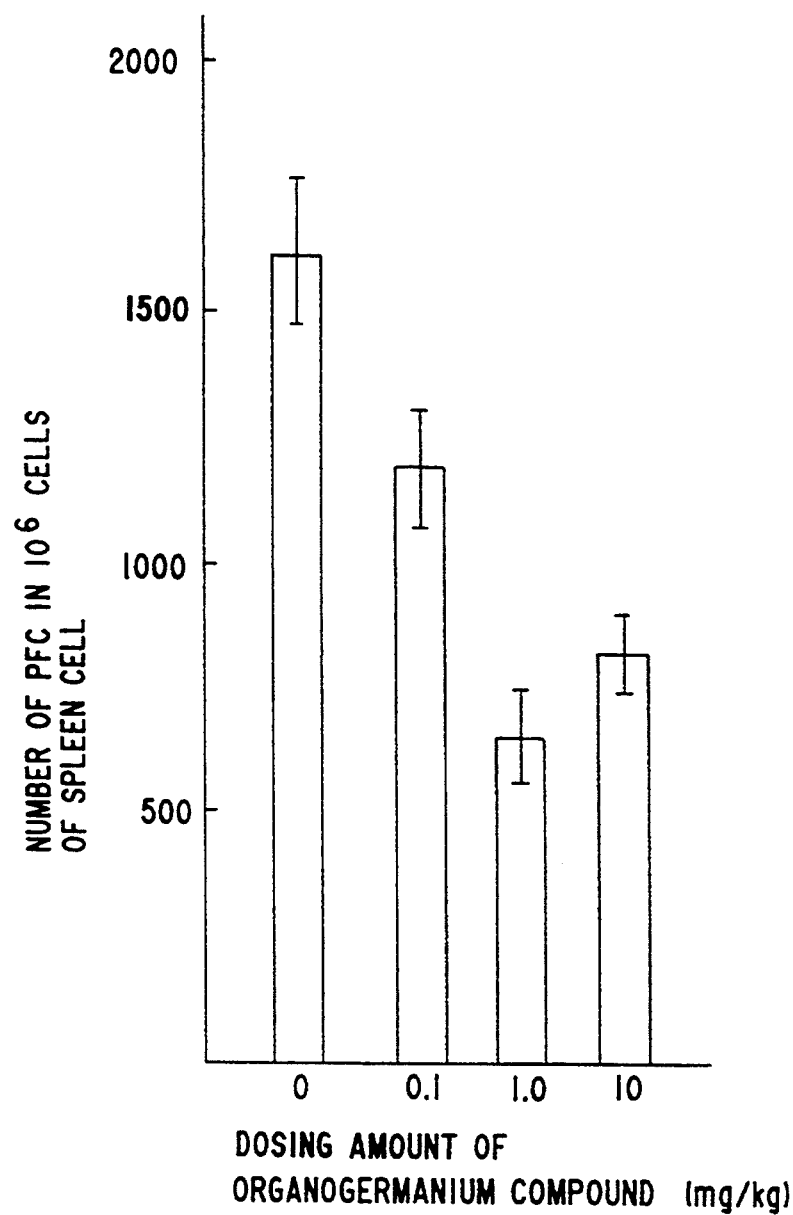

Results in the experimental group sensitized with $2 \times 10^8$ corpuscles of SRBC and the other group sensitized with $2 \times 10^7$ corpuscles of SRBC are shown in FIGS. 8a and 8b, respectively. From the figures, it can be seen that there is a tendancy to decrease spleen cell PFC in the former group but to increase it in the latter group.

These facts apparently show that the organogermanium compound has an immunity adjusting action.

PHARMACOLOGICAL TEST EXAMPLE 2

Influence of Organogermanium Compound on Antibody Production Ability in Cancered Mouse a) Object Similar to the object as referred to in the Pharmacological Test Example 1.

b) Operation $2 \times 10^6$ cells of a mouse tumor cell (Sarcoma 180) were implanted under the skin of a side part of ICR male mice to form a solid cancer. The organogermanium compound (Compound No. 1 in Table 1) dissolved in 4% cattle serum albumin solution was orally dosed to the cancered mice for 5 days, after 9 days had elapsed from the implantation, $2 \times 10^8$ corpuscles of SRBC were injected in a tail vein of the mice for sensitization. After 4 days from the sensitization, spleen cells were extracted to measure of PFC therein, which was used as an index of the antibody productivity.

c) Results and consideration

Figure 9:
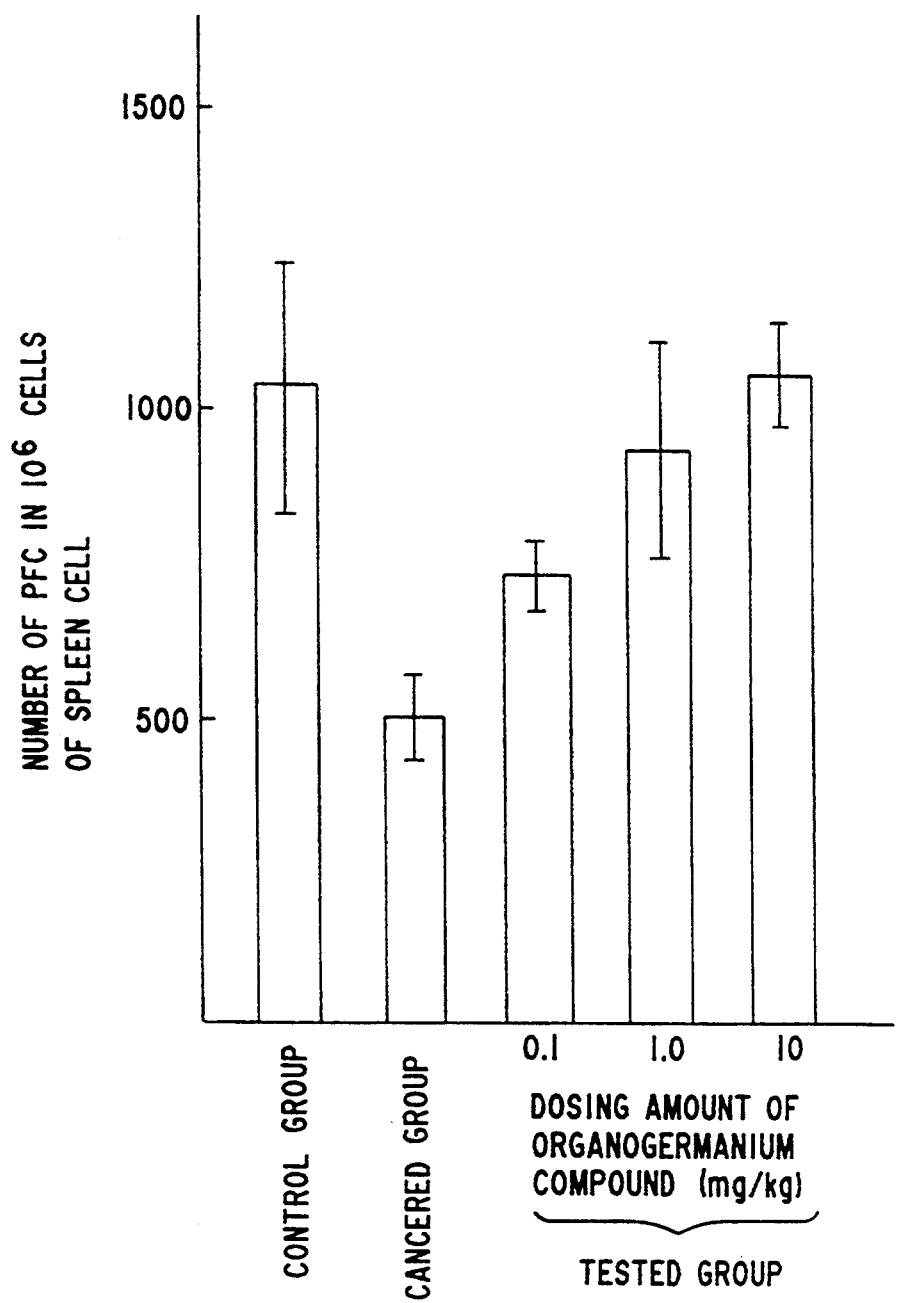
FIG. 9 is a graph showing the influence of the compound on the ability to produce antibodies in cancered mice.

Results are shown in FIG. 9. As seen from the figure, it has been found that the ability to produce antibodies is reduced due to generation of the cancer, but by dosing the organogermanium compound, the ability to produce antibodies recovers towards a normal level, depending on a dosing amount of the compound.

By taking this result, and the result as shown in FIG. 8a into consideration, it is apparent that the organogermanium compound develops an immunity adjusting action.

PHARMACOLOGICAL TEST EXAMPLE 3

Influence of the Organogermanium Compound on the Ability to Produce Antibodies in a Culture System for Mouse Lymphocyte a) Object Influence of the organogermanium compound (Compound No. 1 in Table 1) on SRBC is checked on a culture system of lymphocytes extracted from NZB/W $F^1$ mice who generate a self immunity disease due to functional reduction of suppressor T cells, as well as normal BALB/C mice.

b) Operation

Spleen lymphocytes were extracted from NZB/W $F^1$ male mice (age, 14–15 weeks) and BALB/C male mice (age, 10–13 weeks), washed with a Hanks solution, dispersed through a 100 mesh filter and then washed twice with the Hanks solution. The resulting lymphocytes were dispersed in a 10% fetal calf serum to which was added BPMI 1640 culture medium (including 2-mercaptoethanol in $5 \times 10^5$ M) and containing the organogermanium compound, and the lymphocyte concentration of the dispersion was adjusted with a Turk solution into $1.2 \times 10^7$ corpuscles/ml.

For comparison, SRBC was washed twice with Hanks solution and then dispersed in a manner similar to the above into the 10% fetal calf serum to which was added RPMI culture medium containing the organogermanium compound, and the concentration of the SRBR was adjusted into $1.2 \times 10^7$ corpuscles/mi.

Each 0.5 ml of said lymphocyte suspended medium and said SRBC suspended medium was sampled and mixed. The mixture was charged in a microplate and cultivated for 4 to 5 days at 37° C. under 5% $CO_2$. Thereafter, an anti-SRBC antibody produced cell number was measured by the slide method, as a plague forming cell number.

c) Results and consideration

Figure 10A:
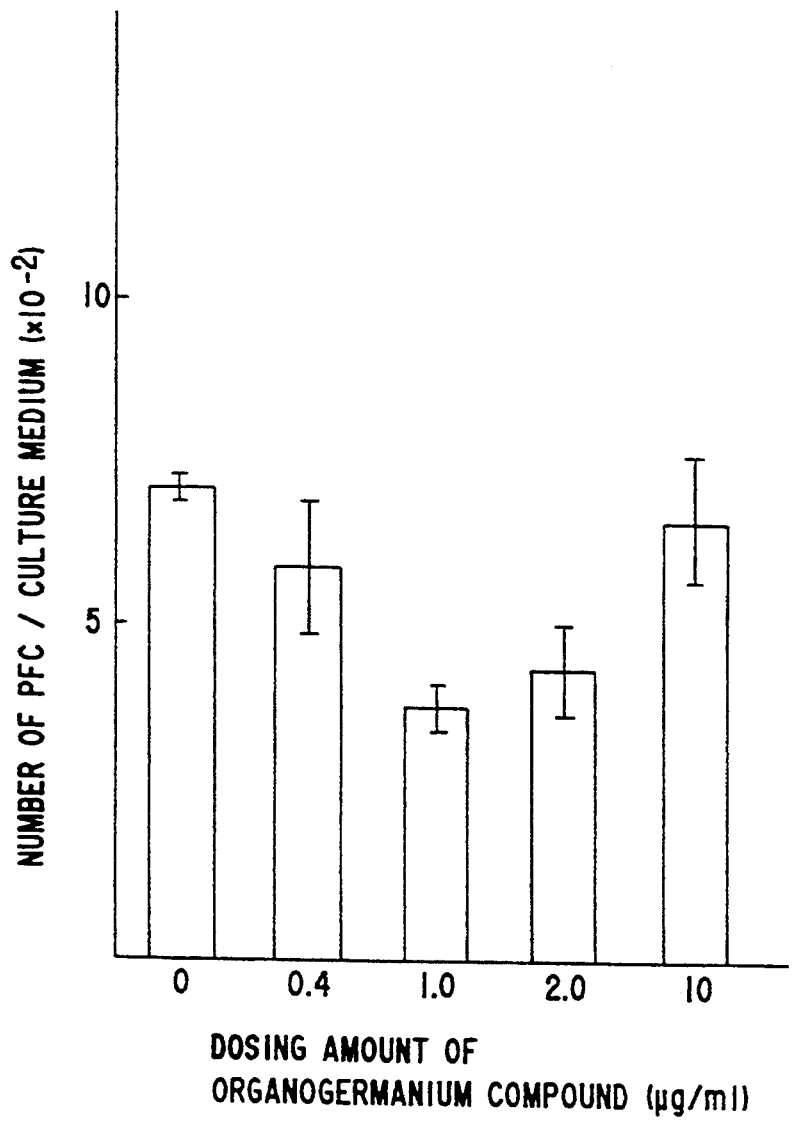
FIGS. 10a and 10b are graphs showing the influence of the compound on the ability to produce antibodies in NZB/W $F_1$ mice and BALB/C mice, respectively.
Figure 10B:
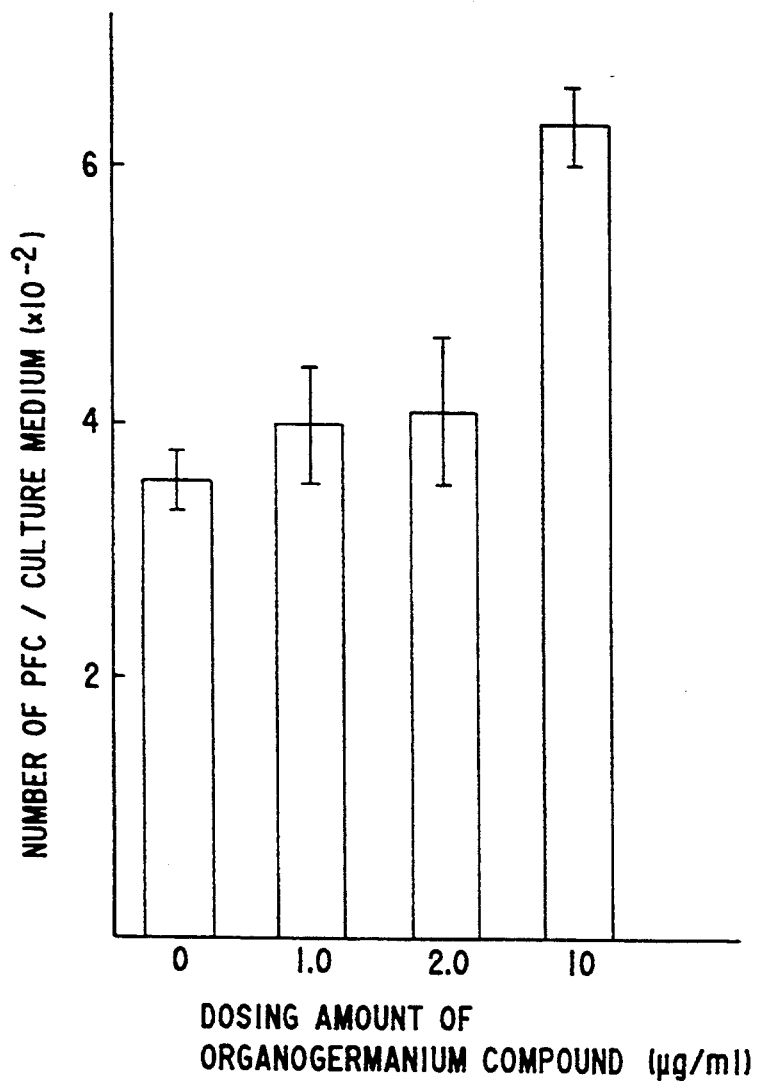

Results are shown in FIGS. 10a and 10b. From the figures, an inhibition in antibody production ability is recognized on the NZB/W $F^1$ mouse lymphocytes when the organogermanium compound is added in the amount of 1 to 2 μg/ml (FIG. 10a), but on the BALB/C mouse lymphocytes, no change was recognized in antibody producing function by adding the organogermanium compound in such amount. On the contrary, an acceleration of the function can be seen when the compound is added in the amount of 10 μg/ml (FIG. 10b).

These results also show apparently that the pharmacological action of the organogermanium compound to the immunity system is an immunity adjusting one.

PHARMACOLOGICAL TEST EXAMPLE 4

Action of Organogermanium Compound to Positive Arthus Reaction in Guinea Pig a) Object For studying the usability of the organogermanium compound (Compound No. 1 in Table 1) to an allergic parietitis, the action thereof to an active Arthus reaction in guinea pig is checked.

b) Operation

To 2% egg albumin solution, the same amount of Freund's complete adjuvant was added to prepare an emulsion. The emulsion was injected in 4 times by one time/week to Hartley male guinea pigs at a heel, under the skin and in the femoralis muscle, for sensitization. After 10 days from the final sensitization, 0.1 ml of 1% egg albumin solution was injected under the skin of the back to measure the area of resulting edema. The organogermanium compound was orally dosed for 30 days from the first sensitization in an amount of 0.1, 1.0 and 10 mg/kg/day.

c) Results

Figure 11:
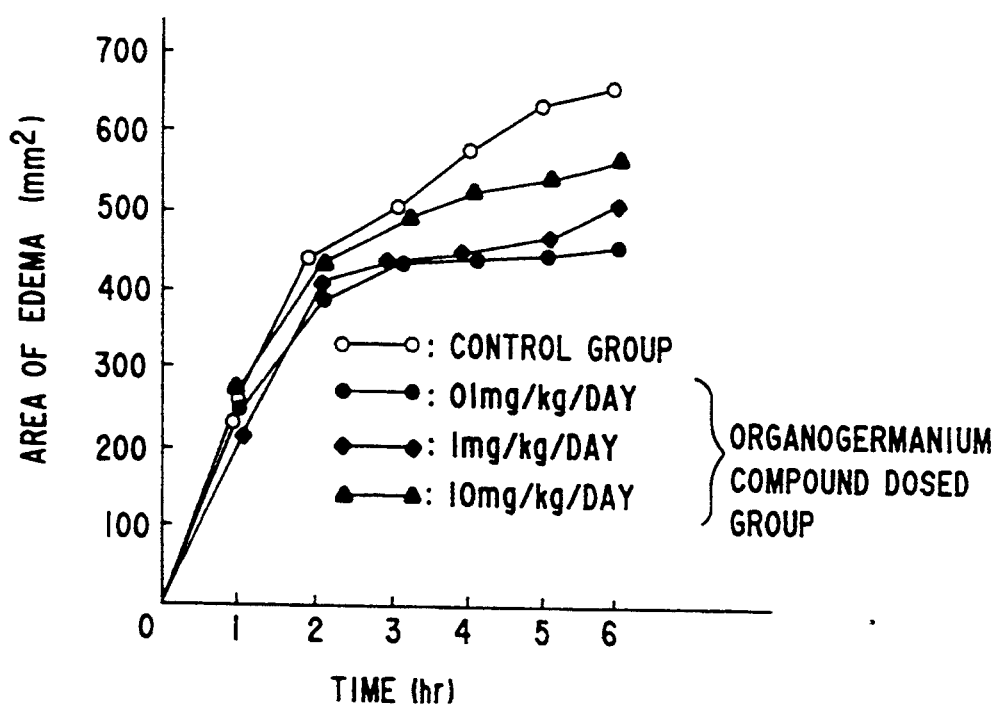
FIG. 11 is a graph showing the influence of the compound on positive Arthus reaction in guinea pigs.

Each change in the edema area is shown in FIG. 11. From the figure, a recognizable inhibition of the phlegmasia can be found in the groups to which the organogermanium compound was dosed in an amount of 0.1 and 1 mg/kg/day, respectively.

PHARMACOLOGICAL TEST EXAMPLE 5

Action of Organogermanium Compound to Adjuvant Arthritis a) Object

The effect of the organogermanium compound (Compound No. 1 in said Table 1) to the prevention of adjuvant arthritis is checked.

b) Operation 0.05 ml of an adjuvant (prepared by suspending 0.6 mg of micobacteriumbutircum into 0.05 ml of liquid paraffin) was injected under the skin of a hind leg heel in S.D. male rats. After 1, 3, 5, 7, 21, and 28 days from the adjuvant dosage, the volume of the dosed and non-dosed legs was measured to determine a ratio of the edema.

The organogermanium compound was orally dosed for 28 days after the adjuvant dosage, in an amount of 1, 10 and 100 mg/kg/day, respectively.

c) Results and consideration

Figure 12:
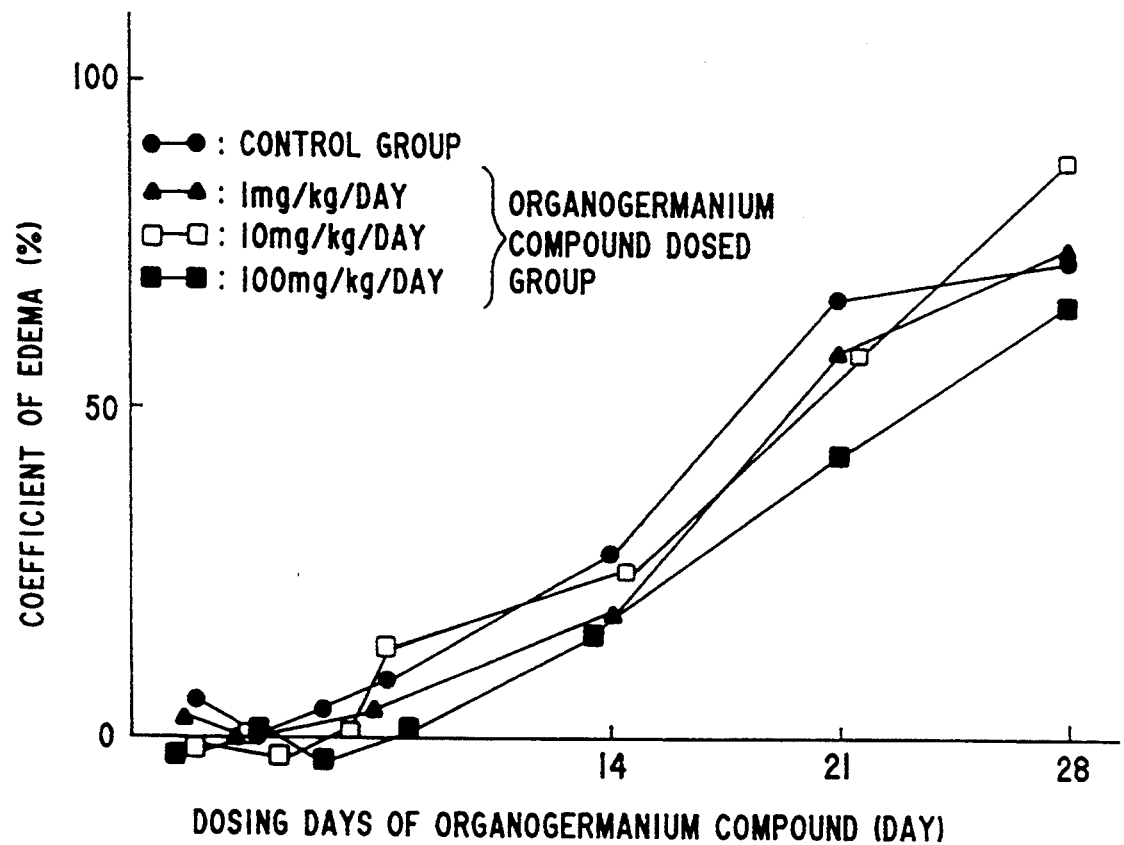
FIG. 12 is a graph showing the influence of the compound on adjuvant arthritis in rats.

Results are shown in FIG. 12. From the figure, an inhibition effect to a secondary phlegmasia after 14 to 28 days can be recognized in the group to which the organogermanium compound was dosed in the amount of 100 mg/kg/day.

REFERENCE 1

Preparation of Stabilized Polymer Composition

Into a 0.5% aqueous solution of gelatin was added 3-oxygermylpropionic acid (Compound 1, Table 1) in an amount to produce a 0.5% (w/v) solution. The mixture was stirred until completely dissolved and the solution was freeze dried to obtain a stabilized polymeric composition.

REFERENCE EXAMPLE 2

Preparation of a Stabilized Polymer Composition

Into a 9% aqueous solution of lactose was added 3-oxygermylpropionic acid (Compound 1, Table 1) in an amount sufficient to produce a 1% (w/v) solution and the mixture was stirred until completely dissolved. The solution was freeze dried to obtain the desired stabilized polymeric composition.

REFERENCE EXAMPLE 3

Preparation of Stabilized Polymer Composition

A stabilized polymer composition was obtained in the same manner as in reference Example 2, except that the starting solution was a 0.5% aqueous solution of hydroxypropylcellulose and the solution was spray-dried.

REFERENCE EXAMPLE 4

Preparation of Stabilized Polymer Composition

A stabilized polymer composition was obtained in the same manner as in reference example 3, except that the starting solution was a 0.5% aqueous solution of hydroxypropylmethylcellulose.

PHARMACEUTICAL AGENT PREPARATION EXAMPLE 1

Injection

To 0.1% solution of sodium carboxymethylcellulose, the organogermanium compound (Compound No. 1 in Table 1) was added to make a concentration of the organogermanium compound 1.5% and then mannitol was made into 2%. The resulting solution was sterilized by filtration, 2 ml filled into each vial, and freeze dried to prepare a powder for preparing an injection.

The powder can be dissolved into isotonic sodium chloride before use.

PHARMACEUTICAL AGENT PREPARATION EXAMPLE 2

Lotion for External Application

The organogermanium compound (Compound No. 1 in Table 1) was added into a 0.5% solution of polyvinylpyrrolidone and dissolved therein to make the concentration of the organogermanium compound 0.1%.

This solution can directly be applied on skin or mucosa for a therapeutic purpose.

PHARMACEUTICAL AGENT PREPARATION EXAMPLE 3

Cream for External Application

The organogermanium compound (Compound No. 1 in Table 1) was added into a 4% solution of bovine serum albumin and dissolved therein to bring the concentration of the organogermanium compound to 1.0%, and then the solution was freeze dried. This freezed dry powder composition was mixed with excipient in a following prescription to prepare a cream agent (ointment).

| | |
|---|---|
| the powder composition | 0.5 (g) |
| diethyl sebacate | 8.0 |
| spermaceti | 5.0 |
| sodium polyoxyethyleneoleyletherphosphate | 6.0 |
| sodium benzoate | 0.5 |
| petrolatum | a sufficent quantity |
| Total | 100 (g) |

PHARMACEUTICAL AGENT PREPARATION EXAMPLE 4

Suppository

The freezed dry composition of Pharmaceutical Agent Preparation Example 3 was dispersed in melted higher fatty acid glycerides in the following amount ratio and suppositories were made from the dispersion by a conventional method.

| | |
|---|---|
| the Powder Composition | 60 (mg) |
| fatty base (cacao butter) | 1640 |
| | 1700 (mg)/piece |

PHARMACEUTICAL AGENT PREPARATION EXAMPLE 5

Tablet

The organogermanium compound (Compound No. 1 in Table 1) was added and dissolved in a 1% aqueous solution of pepsin, to make the concentration of the organogermanium compound 1% and then the solution was freeze dried.

The freezed dried composition was mixed with excipients in the following prescription to prepare tablets in a conventional method.

| | |
|---|---|
| the powder composition | 60 (mg) |
| lactose | 90 |
| calcium carboxymethylcellulos | 7 |
| light anhydrous silicic aced | 1 |
| magnesium stearate | 7 |
| | 165 (mg)/tablet |

PHARMACEUTICAL AGENT PREPARATION EXAMPLE 6

Capsule

The freezed dried composition of Pharmaceutical Agent Preparation Example 5 was mixed with other ingredients in the following prescription and this mixture as filled into each hard gelatin capsule, by a conventional method, to prepare capsuled agent.

| | |
|---|---|
| the powdered composition | 30 (mg) |
| lactose | 107 |
| hydroxypropylmethylcellulose | 2 |
| magnesium stearate | 1 |
| | 140 (mg)/capsule |

PHARMACEUTICAL AGENT PREPARATION EXAMPLE 7

Capsule

Capsules were prepared in a conventional manner using the following ingredients in the listed amounts:

| | |
|---|---|
| Stabilized polymer composition (Ref. Ex. 1) | 40 (mg) |
| lactose | 107 |
| hydroxypropylmethylcellulose | 2 |
| magnesium stearate | 1 |
| | 150 mg/capsule |

PHARMACEUTICAL AGENT PREPARATION EXAMPLE 8

Tablet

Tablets were prepared in a conventional manner by compounding the following gradients in the listed amounts and conventionally tableting same:

| | |
|---|---|
| Stabilized polymer composition (Ref. Ex. 2) | 100 mg |
| lactose | 50 |
| calcium carboxymethylcellulose | 7 |
| light anhydrous silicic acid | 1 |
| magnesium stearate | 7 |
| | 165 mg/tablet |

PHARMACEUTICAL AGENT PREPARATION EXAMPLE 9

Powder

Powders were prepared by mixing the following ingredients in the amounts indicated:

| | |
|---|---|
| stabilized polymer composition (Ref. Ex. 3) | 60 mg |
| lactose | 940 |
| | 1000 mg/pkg |

PHARMACOLOGICAL AGENT PREPARATION EXAMPLE 10

Granule

Granules were obtained in a conventional wet-granulation method using ethanol and water. The ingredients and amounts are listed as follows:

| | |
|---|---|
| stabilized polymer composition (Ref. Ex. 4) | 55 mg |
| lactose | 685 |
| corn starch | 250 |
| hydroxypropylcellulose | 10 |
| | 1000 mg/pkg |

IN VIVO UTILIZATION EXAMPLE 1

The external cream agent obtained in Pharmaceutical Agent Preparation Example 3 was given to 20 volunteers, who had a red swelling due to being stung by an insect, food allergy, pain or itching due to piles or the like local disease, to use the same, as required. After a specified time period, a questionnaire was distributed and analyzed to obtain the results shown in the following Table 3. As seen from the Table, almost all persons answered to the effect that the cream agent has a curing effect.

IN VIVO UTILIZATION EXAMPLE 2 a) Objects

Effects of the organogermanium compound are checked by giving the capsule obtained in Pharmaceutical Composition Preparing Example 7 to 6 patients infected by HIV (Human Immunodeficiency Virus), who are male hemophiliacs (Age: 6 to 22 years old) recognized as asymptomatic carriers, and among them 5 patients were positive to HIV and 1 patient was negative to HIV.

b) Operations and Items of Inspection

To each patient, the capsule was given in a dose of 80 mg/day for the patients of 10 years old or over and 40 mg/1 day for the patients less than 10 years old, for 9 months. The number of blood lymphocytes, $OKT_4$-value, $OKT_8$-value and OKT4/8 ratio, as well as the change in the virus marker (HIV, HIV antigen and HIV antibody) in blood of the patients were monitored. The separation of the HIV was carried out in accordance with the CDC (Communicable Disease Center) method, and the measurement of the HIV antigen was carried out using the Western blotting method.

c) Results and consideration i) Lymphocytes

No noticeable change has been observed on the number of lymphocytes, as shown below:
Before: 2430±311/μl, and
After 6 months: 2349±312/μl.

ii) OKT$_4$-value

Change in the OKT4-value is as follows:
Before: 463±64/μl,
After 2 months: 549±89/μl, and
After 6 months: 629±97/μl.

Although this shows a certain increasing tendency in the value, it has been found that a value in the normal range at the time of first measurement shall not so change in level through the testing time period. A value at a lower level at the first stage apparently increases, and a value at a higher level at the first stage apparently decreases.

iii) OKT$_8$-value

Change in the OKT$_8$-value is as follows:
Before: 1303±174/μl, and
After 6 months: 1154±153/μl.

Although this shows a certain decreasing tendency in the value, it has been found that the value in each group shows the tendencies similar to those in OKT4-value.

iv) OKT$_{4/8}$ ratio

Change in the ratio is as follows:
Before: 0.36±0.03,
After 1 month: 0.42±0.02,
After 3 months: 0.51±0.06, and
After 6 months: 0.54±0.05.

The shows a slow increase in the ratio.

From the above i) to iii), it has been estimated that the organogermanium compound shows an anti-vital action through the immune system and more particularly, acts on T-cells and MO to adjust the immune response.

v) change in virus marker on HIV positive patients

Through the testing period of time over 9 months, no change has been observed on 2 persons among 5 HIV positive patients, but HIV disappeared in 3 other persons, as a result of the dosage of the compound over 6 months, as shown in the Table given below.

Some increase in appetite and body weight have been recognized on 2 persons, but clinical observation did not show any side-effect.

| Patient | Item | Week(s) -5 | Week(s) 0 | Week(s) 2 | Months 6 | Months 7 | Months 9 |
|---|---|---|---|---|---|---|---|
| A | HIV separation |  | + | + | − | − | − |
|  | HIV antigen |  | − | − | − | − | − |
|  | HIV antibody |  | + | + | + | + | + |
| B | HIV separation | + | + | + | − | − | − |
|  | HIV antigen | + | + | + | + | + | + |
|  | HIV antibody | + | + | + | + | + | + |
| C | HIV separation |  | + | + | − | − | − |
|  | HIV antigen |  | + | + | + | + | + |
|  | HIV antibody |  | + | + | + | + | + |

In the following Pharmacological Test Examples and In Vivo Utilization Examples, capsules as prepared by Pharmaceutical Agent Preparation Example 6 were employed, although an amount of the effective organogermanium compound may have been varied.

PHARMACOLOGICAL TEST EXAMPLE 6

Test on Safety (1) Single dose test

A single dose test was carried out on healthy adult persons (5 men). The amount of dose was firstly set to 15 mg/body as the effective compound, which amount corresponds to 1/12000 of LD$_{50}$ for beagle dog, which is one of the sensitive animals, and to ¼ of 1 mg/kg which has been suggested as most effective in pharmaceutical tests using experimental animals.

The capsule was dosed by each person when his stomach was empty to check stethoscopy, subjective symptoms, and to carry out biological examinations, biochemical examinations with use of serum, endocrinological examinations, ufoscopy, and to take a cardiogram, but no abnormality was found in any of the tests and examinations.

While confirming the safety of the test compound, the amount of dose was gradually increased to 30, 60, 120 and 240 mg/body and said tests and examinations were carried out, but no abnormality had been found in any case.

(2) Frequentative dose test

Healthy adult persons were classified into following 3 groups (5 men in each group) and a capsule was dosed by them in a following manner.

(a) Group A 60 mg×3 times/day, between meals,
(b) Group B 60 mg×2 times/day, fasting, and
(c) Group C 60 mg×3 times/day, after a meal.

Results of the tests and examinations as given in preceding Item (1) showed no abnormality in all groups.

(3) Continuous dose test

A capsule containing 60 mg as the effective organogermanium compound was dosed by each of healthy adult persons (5 men) for a continuous 7 days at a dose rate of 3 times/day, to carry out the tests and examinations as given in preceding Item (1), but no abnormality was found in any person.

(4) Single dose test on patients

A single dose test was carried out on the following patients by giving them a capsule, containing 60 mg as the effective organogermanium compound to administer the same, when the stomach of each person was empty. The tests and examinations as given in preceding Item (1) were carried out, but no abnormality was found in any case.

(a) 4 persons infected with chronic non A non B hepatitis, and
(b) 1 person infected with acute non A non B hepatitis.

(5) Kinetics of drug in plasma

A capsule containing various amount of effective organogermanium compound were dosed to each of healthy adult persons to check kinetics of the drug. Results showed that the concentration of the drug reaches its maximum level after 3 hours from the administration, and AUC increases as the amount of dose increases. The excretion ratio of the drug in urine was 30–50% in cases of any dose. The concentration of the drug in plasma on the first day of the continuous dose test showed a value in the same level same as that on the 7th day of the test. This suggests that the drug does not show a tendency to accumulate.

Regarding to kinetics of the drug in plasma of persons infected with non A non B hepatitis, it was observed that AUC, $C_{max}$ and excretion ratio of drug in urine tended to increase in comparison with those of healthy persons, as shown in the following Table 4, but the degree of increases lies in a range of fluctuations depending on different individuals. Therefore, it has been judged that the influence of the hepatitis on pharmakinetics of the drug is small.

The following Table 3 shows pharmakinetic parameters of the drug in plasma and excretion ratio of the drug into urine, when the capsule containing 60 mg as the effective organogermanium compound was orally dosed by 5 healthy persons (Group A), 4 persons (Group B) infected with chronic non A non B hepatitis, and 1 person (Group C) infected with acute non A non B hepatitis.

TABLE 3

| Pharmakinetic parameters | Group A | Group B | Group C |
|---|---|---|---|
| $T_{max}$ (hr) | 2.6 ± 0.2 | 3.5 ± 0.5 | 3 |
| $C_{max}$ (μg/ml) | 0.467 ± 0.067 | 0.673 ± 0.123 | 0.387 |
| AUC (μg.hr/ml) | 3.14 ± 0.41 | 4.43 ± 0.50 | 2.42 |
| $K_{el}$ (hr$^{-1}$) | 0.261 ± 0.017 | 0.225 ± 0.020 | 0.183 |
| $t_{\frac{1}{2}}$ (hr) | 2.70 ± 0.18 | 3.17 ± 0.32 | 3.79 |
| Excretion ratio into urine (%) (0–24 hr.) | 34.2 ± 3.9 | 51.3 ± 5.0 | 41.6 |

IN VIVO UTILIZATION EXAMPLE 1

(1) object

Search on effectiveness of the organogermanium compound to chronic B and non A non B hepatitises and preferable amount of dose thereof.

(2) Manner of dose

Experiments on cellular immune response and various experimental models infected with hepatitis show that a preferable amount of oral dose is 1 mg/kg. Therefore, 30 mg, 60 mg and 90 mg/day/body were set. Experimental period of time was set for 12 weeks.

(3) Kind of Examinations (a) Examination of liver functions (GOT, GPT, A 1-P, and γ-GTP), and (b) Examination with use of HBV markers (HBe-Ag, HBe-Ab and DNA-P).

(4) Results

Results are shown in following Table 4A and 4B.

TABLE 4A

| Disease | Chronic B Hepatitis | | |
|---|---|---|---|
| Dose | 30 mg/day | 60 mg/day | 90 mg/day |
| Patients in total | 48 | 37 | 39 |
| Patients for analysis | 46 | 37 | 39 |
| Subjects | | | |
| CAH | 27 | 22 | 29 |
| CIH | 8 | 5 | 5 |
| Unknown | 11 | 10 | 4 |
| General judgement | | | |
| Improvement (slight or more) | 52% (22/42) | 37% (13/35) | 43% (16/37) |
| Safety (quite) | 93% (39/42) | 97% (35/36) | 90% (34/38) |
| Effectiveness (slight or more) | 55% (23/42) | 47% (17/36) | 47% (18/38) |
| Functions of the liver | | | |
| GOT | ↓ * | | |
| GPT | ↓ + | | |
| A 1-P | ↓ * | | |
| γ-GTP | ↓ * | | |
| HBV markers | | | |
| Improvement (slight or more) | 36% + (8/22) | 27% + (4/15) | 15% + (3/20) |
| HBe - Ag (log conversion) | ↓ ** | | |
| HBe - Ab | ↑ * | ↑ + | ↑ ** |
| DNA - P | ↓ + | | |
| Side effect | 8.7% | 2.7% | 7.9% |

TABLE 4A-continued

| Disease | Chronic B Hepatitis | | |
|---|---|---|---|
| Dose | 30 mg/day | 60 mg/day | 90 mg/day |
| | (4/46) | (1/37) | (3/38) |

TABLE 4B

| Disease | Chronic non A non B hepatitis | | |
|---|---|---|---|
| Dose | 30 mg/day | 60 mg/day | 90 mg/day |
| Patients in total | 37 | 34 | 30 |
| Patients for analysis | 36 | 34 | 30 |
| Subjects | | | |
| CAH | 23 | 20 | 15 |
| CIH | 6 | 6 | 5 |
| Unknown | 7 | 8 | 10 |
| General judgement | | | |
| Improvement (slight or more) | 29% (10/34) | 45% (13/29) | 41% (11/27) |
| Safety (quite) | 92% (33/36) | 91% (29/32) | 90% (26/29) |
| Effectiveness (slight or more) | 31% (11/36) | 44% (14/32) | 38% (11/29) |
| Functions of liver | | | |
| GOT | | ↓ ** | |
| GPT | | ↓ * | |
| A 1-P | | ↓ ** | |
| Side effect | 8.3% (3/36) | 8.8% (3/34) | 10.0% (3/30) |

In both Tables 4A and 4B,

**: p<0.01,

*: p<0.05,

+: p<0.10, and

Direction of arrow shows that in change (t-test between mean values before the Examination and after the Examination for 12 weeks.

(5) Consideration

From the results given in above, preferable dose is 30 mg/day/body for the treatment of chronic B hepatitis, and 30–60 mg/day/body for the treatment of non A non B hepatitis.

IN VIVO UTILIZATION EXAMPLE 2

(1) Object

Search on utility or effectiveness of the organogermanium compound on patients who are infected with chronic B hepatitis, or with non A non B hepatitis, and show "positive" to HBe antigen as well as a preferable amount of dose thereof.

(2) Manner of dose

The amount of dose has been set as follows, by taking the results given in In Vivo Utilization Example 1 into consideration.

To patents with chronic B hepatitis (a) 30 mg/day/body showing most preferable data in effectiveness, and (b) 15 mg/day/body (half amount).

To patients with non A non B hepatitis (a) 60 mg/day/body showing most preferable data in effectiveness, (b) 30 mg/day/body showing effectiveness in some Experiments, and (c) 15 mg/day/body (for taking control data).

Experimental period of time was set for 12 weeks.

(3) Kind of Examinations (a) Examination of liver functions (GOT, GPT, total bilirubin, LDH, γ-GTP, and γ-globulin), and (b) Examination with use of HBV marker (HBe-Ag).

(4) Results

Results are shown in following Table 5A and 5B.

TABLE 5A

| Disease | Chronic B hepatitis | | | |
|---|---|---|---|---|
| Dose | 15 mg/day | 30 mg/day | Test | |
| Patients in total | 46 | 46 | U | $x^2$ |
| Patients for analysis | 38 | 40 | — | NS |
| Subjects | | | | |
| CAH | 26 | 31 | | |
| CIH | 9 | 5 | — | NS |
| Unknown | 3 | 4 | | |
| General judgement | | | | |
| Improvement (slight or more) | 36% (12/33) | 62% (21/34) | + | + |
| Safety (quite) | 97% (33/34) | 94% (33/35) | NS | NS |
| Effectiveness (slight or more) | 38% (13/34) | 60% (21/35) | + | NS |
| Functions of liver | | | | |
| GOT | | ↓ *** | *(15<30) | |
| GPT | | ↓ *** | +(15<30) | |
| LDH | | ↓ * | | |
| HBe - Ag (log conversion) | | ↓ + | | |
| Side effect | 2.9% (1/34) | 5.7% (2/35) | — | NS |

TABLE 5B

| Disease | Chronic non A non B hepatitis | | | |
|---|---|---|---|---|
| Dose | 15 mg/day | 30 mg/day | 60 mg/day | Test |
| Patients in total | 44 | 42 | 46 | $x^2$ |
| Patients for analysis | 38 | 38 | 42 | NS |
| Subjects | | | | |
| CAH | 24 | 25 | 33 | |
| CIH | 7 | 11 | 7 | NS |
| Unknown | 7 | 2 | 2 | |
| General judgement | | | | |
| Improvement (slight or more) | 36% (11/31) | 37% (13/35) | 57% (21/37) | NS |
| Safety (quite) | 91% (29/32) | 94% (34/36) | 95% (35/37) | NS |
| Effectiveness (slight or more) | 33% (11/33) | 36% (13/36) | 55% (21/38) | NS |
| Functions of liver | | | | |
| GOT | | | ↓ * | |
| GPT | | | ↓ ** | |
| Total bilirubin | ↓ * | | ↓ * | |
| γ-GPT | ↓ + | | ↓ * | |
| γ-Globulin | | | ↓ * | |
| Side effect | 9.4% (3/32) | 5.6% (2/36) | 5.4% (2/37) | NS |

In both Tables 5A and 5B,
***: p<0.001,
**: p<0.01,
*: p<0.05,
+: p<0.10, and
Direction of arrow shows that in change (t-test between mean values before the Examination and after the Examination for 12 weeks).

(5) Consideration

From the results given above, preferable dose is 30 mg/day/body for the treatment of chronic B hepatitis, and 60 mg/day/body for the treatment of non A non B hepatitis.

IN VIVO UTILIZATION EXAMPLE 3

(1) Object

Utility or effectiveness of the organogermanium compound is checked in comparison with that of a placebo as a control.

(2) Ground selected the placebo as the control

Interferons have widely been accepted as drugs for curing chronic hepatitis, but those are injectionally dosed. On the contrary, the organogermanium compound is orally dosed. In recent years, some oral medicines for curing liver diseases have been developed and the effectiveness thereof has been evaluated by using a placebo as its control. Therefore, the "placebo" is selected as the control for the evaluation of the organogermanium compound in question.

(3) Amount of dose

The amount of dose had been set as follows, by taking the results given in In Vivo Utilization Example 2 into consideration.

(a) To patients with chronic B hepatitis: 30 mg/day/body.

(b) To patients with non A non B hepatitis: 60 mg/day/body.

Experiment period of time was set for 16 weeks for the patients with chronic B hepatitis and for 12 weeks for the patients with non A and non B hepatitis.

(4) Results

Results are shown in following Table 6A and 6B

TABLE 6A

| Disease | Chronic B hepatitis | | | |
|---|---|---|---|---|
| Compound | Test compound | Placebo | Test | |
| Patients in total | 104 | 89 | U | $x^2$ |
| Patients for analysis | 101 | 81 | — | NS |
| Subjects | | | | |
| CAH | 80 | 62 | | |
| CIH | 15 | 14 | — | NS |
| Unknown | 6 | 5 | | |
| General judgement | | | | |
| Improvement (Doc. on duty) | 58% (15/95) | 31% (21/68) | *** | ** |
| Improvement (sec. judgement) | 54% (51/95) | 29% (20/68) | *** | ** |
| Improvement (HBe Ag-Ab) | 51% (40/79) | 25% (13/52) | NS | NS |
| Improvement (self) | 53% (16/30) | 40% (13/52) | NS | NS |
| Improvement (objective) | 10% (3/30) | 13% (4/30) | NS | NS |
| Improvement (general) | 66% (62/94) | 39% (25/65) | *** | ** |
| Safety (quite) | 98% (93/95) | 90% (64/71) | * | + |
| Effectiveness (slight or more) | 63% (60/96) | 34% (25/74) | *** | *** |
| Functions of liver | | | | |
| GOT | ↓ *** | | + (S>P) | |
| GPT | ↓ *** | | * (S>P) | |
| γ-GPT | ↓ ** | | | |
| A/G | ↑ ** | | | |
| Serum albumin | ↑ + | | | |
| γ-Globulin | ↓ *** | | + (S>P) | |
| Total cholesterol | ↑ * | | * (S>P) | |
| TTT | ↓ *** | | | |
| ZTT | ↓ ** | | | |
| HBV marker | | | | |
| HBe - AG (log conversion) | ↑ *** | | * (S>P) | |
| HBe - Ab | ↑ * | | * (S>P) | |
| Side effect | 3.2% (3/95) | 11.3% (8/71) | — | NS |

TABLE 6B

| Disease | Chronic non A non B hepatitis | | | |
|---|---|---|---|---|
| Compound | Test compound | Placebo | Test | |
| Patients in total | 101 | 97 | U | $x^2$ |
| Patients for analysis | 93 | 92 | — | NS |
| Subjects | | | | |
| CAH | 74 | 71 | | |
| CIH | 14 | 15 | — | NS |

TABLE 6B-continued

| Disease | Chronic non A non B hepatitis | | |
|---|---|---|---|
| Compound | Test compound | Placebo | Test |
| Unknown | 5 | 6 | |
| General judgement | | | |
| Improvement (Jud. by Doc.) | 56% (44/79) | 29% (24/84) | *** *** |
| Improvement (sec. judgement) | 51% (40/79) | 26% (22/84) | *** ** |
| Improvement (self) | 50% (14/28) | 48% (15/31) | NS NS |
| Improvement (objective) | 8% (2/26) | 10% (3/29) | NS NS |
| Improvement (general) | 59% (46/78) | 32% (26/82) | *** *** |
| Safety (quite) | 89% (74/83) | 93% (77/83) | NS NS |
| Effectiveness (slight or more) | 50% (60/96) | 29% (25/74) | ** ** |
| Functions of liver | | | |
| GOT | ↓ *** | | ** (S>P) |
| GPT | ↓ *** | | ** (S>P) |
| γ-GPT | ↓ * | | * (S>P) |
| A/G | ↑ + | ↑ + | |
| Serum albumin | ↓ ** | | |
| ZTT | | ↓ + | |
| Side effect | 12.0% (10/83) | 7.2% (6/83) | — NS |

In both Tables 6A and 6B,
***: $p < 0.001$,
**: $p < 0.01$,
*: $p < 0.05$,
+: $p < 0.10$, and
Direction of arrow shows that in change (t-test between mean values before the Examination and after the Examination for 12 weeks).

IN VIVO UTILIZATION EXAMPLE 4

(1) Object

A capsule containing the organogermanium compound was dosed to patients infected with chronic B hepatitis over a long period of time at a rate of 30 mg/day/body as the effective compound to check safety and effectiveness.

(a) Number of patients for analysis: 34 persons.
(b) Mean dosing period of time: 55 weeks.
(c) Number of patients who continuously dose over 48 weeks: 26 persons.

(2) Results

A ratio of improvement in functions of liver reached 63% by the judgement of a doctor or physician in charge, and 59% by the secondary judgement of a committee, as the base of at least slight improvement.

Ratios of improvement in liver tissue are shown in the following Table 7. The improvements in liver tissue has good correlation with improvements in liver functions.

TABLE 7

| State | Patient | Improvement (%) | |
|---|---|---|---|
| | | ≧middle | ≧slight |
| Liver lobule | | | |
| Degenerative necrosis in cell | 24 | 16.7 | 37.5 |
| Cobwebby necrosis | 24 | 16.7 | 37.5 |
| Bridging necrosis | 9 | 22.2 | 33.3 |
| Fatty degeneration | 11 | 0 | 9.1 |
| Ballooning of cell | 4 | 0 | 50.0 |
| Mobilization image of Kupfer cell | 24 | 16.7 | 41.7 |
| Glisson's capsule | | | |
| Round cell infiltration | 24 | 0 | 12.5 |
| Piecemeal necrosis | 17 | 17.6 | 29.4 |
| Fibrosis | 23 | 8.7 | 17.4 |
| Moderation of lobule | 15 | 0 | 6.7 |
| Evaluation | | 3/24 (12.5%) | 10/24 (41.7%) |

Among 23 patients showing "positive" to HBe antigert, 3 patients changed to SC (seroconversion) and another 3 patients changed to SN (seronegative) and thus ratio of disappearance of HBe antigen reached 26%.

IN VIVO UTILIZATION EXAMPLE 5

A capsule containing the organogermanium compound was dosed to 40 patients infected with chronic B hepatitis, who showed "positive" to HBe antigen or "negative" to HBe antigen ("Positive" to HBe antibody), for 16 weeks by 30 mg/day/body as the effective compound to check utility or effectiveness.

(1) Improvement in functions of liver

Ratio of improvement in functions of liver showed 30%, based on middle or more improvement, and 50%, based on slight or more improvement. There was found no significant difference between the HBe antigert positive and negative groups.

(2) Examination of DNA-polymerase (DNA-P)

4 patients (14%) changed from "positive" to "negative" at the time of end of the experiment.

The value of DNA-P reduced to 50% or more in 14 patients (50%), in comparison with the value before the experiment. The value reduced to 25% or more in 19 patients (68%). In general, a significant reduction of the value was found in the 12th and 16th week.

(3) HBe antigen and antibody

2 Patients among 33 HBe antigen positive group changed to SC. A significant reduction of HBe antigen was found after 8 and 12 weeks from initial dose. Significant increase of HBe antibody was found after 8 weeks from the initial dose.

(4) Lymph cell sub-set by Two-color analysis

A significant reduction can be found in suppressor T lymph cell and other CD8 positive cells.

IN VIVO UTILIZATION EXAMPLE 6

(1) Object

A capsule containing the organogermanium compound was dosed to patients infected with chronic non A non B hepatitis over a long period of time to check safety and effectiveness of the organogermanium compound.

(a) Number of patients for analyzation: 68 persons.
  Group A: 39 persons (dose; 30 mg/day/body), and
  Group B: 29 persons (dose; 60 mg/day/body).
(b) Mean dosing period of time
  Group A: 50 weeks, and
  Group B: 47 weeks.
(c) Number of patients who continuously dose over 48 weeks
  Group A: 29 persons, and
  Group B: 18 persons.
(2) Results Results are shown in the following Tables 8 (improvement in functions of liver) and 9 (improvement in liver tissue).

TABLE 8

|  | 30 mg/day | 60 mg/day | Test |
| --- | --- | --- | --- |
| Remarkably improved | 2 | 3 | Zo = 2.121 |
| Middle improved | 2 | 4 | p = 0.034 |
| No change | 20 | 11 | (*) |
| Getting worse | 3 | 0 |  |
| Total | 35 | 26 |  |
| Ratio of improvement |  |  |  |
| Middle or more | 11.4% | 34.3% | p = 0.223 |
| Slight or more | 26.9% | 57.7% | p = 0.119 |
|  |  |  | (**) |

In Table 8,
*: Mann-Whitney's U-test, and
**: Fisher's direct calculation method.

TABLE 9

| State | Patient | Improvement (%) ≧middle | ≧slight |
| --- | --- | --- | --- |
| Liver lobule |  |  |  |
| Degenerative necrosis in cell | 17 | 5.9 | 52.9 |
| Cobwebby necrosis | 17 | 5.9 | 52.9 |
| Bridging necrosis | 3 | 0 | 33.3 |
| Fatty degeneration | 9 | 0 | 22.2 |
| Ballooning of cell | 4 | 0 | 0. |
| Mobilization image of Kupfer cell | 16 | 6.3 | 50.0 |
| Glisson's capsule |  |  |  |
| Round cell infiltration | 17 | 0 | 17.6 |
| Piecemeal necrosis | 13 | 0 | 38.5 |
| Fibrosis | 17 | 0 | 5.9 |
| Moderation of lobule | 8 | 0 | 12.5 |
| Evaluation |  | 1/17 (5.9%) | 10/17 (58.8%) |

(3) Consideration

Results shown in Tables 8 and 9 support that a dose of 60 mg/day/body is preferable to treat non A non B hepatitis.

We claim:

1. A method for the treatment of chronic B, and non A non B hepatitis in a person requiring said treatment, comprising administering to the person a pharmaceutical composition which comprises: an effective amount of a stabilized 3-oxygermylpropionic acid polymer composition comprising:

0.01 to 1.0% by weight of a therapeutically effective polymer of the formula

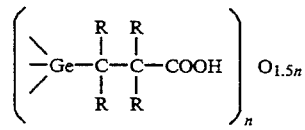

wherein n is an integer of 1 or more, and the R's are the same or different and are: hydrogen, $C_1$–$C_{13}$ alkyl, —COOH, COOR', phenyl,

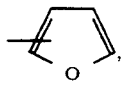

or

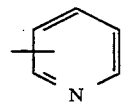

wherein R' is a lower alkyl, 0.5 to 10% by weight of a high molecular weight substance as a stabilizer for the polymer which is selected from the group consisting of gelatin, lactose, hydroxypropylcellulose and hydroxypropylmethylcellulose, and a compatible and pharmaceutically acceptable carrier of the polymer composition.

2. A method as claimed in claim 1, wherein said pharmaceutical composition is administered to the person infected with human B hepatitis.

3. A method as claimed in claim 1, wherein said pharmaceutical composition is administered to the person infected with human non A non B hepatitis.

4. In the method for the treatment of chronic B, and non A non B hepatitis in a person requiring said treatment, comprising:

administering to the person a pharmaceutical composition which comprises:

an effective amount of 0.01 to 1.0% by weight of a therapeutically effective 3-oxygermylpropionic acid polymer composition polymer of the formula:

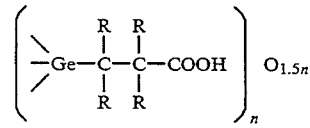

wherein n is an integer of 1 or more, and the R's are the same or different and are: hydrogen, $C_1$–$C_{13}$ alkyl, —COOH, COOR', phenyl,

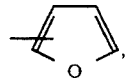

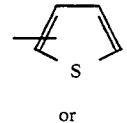

or

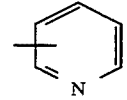

wherein R' is a lower alkyl, and
a compatible and pharmaceutically acceptable carrier of the polymer composition;
the improvement which comprises using said composition wherein said therapeutically effective polymer is stabilized with 0.5 to 10% by weight of a high molecular weight substance as a stabilizer for the polymer which is selected from the group consisting of gelatin, lactose, hydroxypropylcellulose and hydroxypropylmethylcellulose.

5. The improved method as claimed in claim 4 wherein said stabilized composition is administered to a person infected with human B type hepatitis.

6. The improved method as claimed in claim 4 wherein said stabilized composition is administered to a person infected with human non A non B type hepatitis.

* * * * *